(12) United States Patent
Shirai

(10) Patent No.: US 7,988,990 B2
(45) Date of Patent: Aug. 2, 2011

(54) THIN AQUEOUS CATAPLASM

(75) Inventor: Sadanobu Shirai, Takamatsu (JP)

(73) Assignee: Teikoku Seiyaku Co., Ltd., Kagawa-ken (JP)

( * ) Notice: Subject to any disclaimer, the term of this patent is extended or adjusted under 35 U.S.C. 154(b) by 0 days.

(21) Appl. No.: 10/542,932

(22) PCT Filed: Jan. 26, 2004

(86) PCT No.: PCT/JP2004/000641
§ 371 (c)(1),
(2), (4) Date: Jul. 21, 2005

(87) PCT Pub. No.: WO2004/066985
PCT Pub. Date: Aug. 12, 2004

(65) Prior Publication Data
US 2006/0093654 A1    May 4, 2006

(30) Foreign Application Priority Data

Jan. 28, 2003    (JP) ................ 2003-018927

(51) Int. Cl.
*A61L 15/00* (2006.01)
(52) U.S. Cl. ..................... 424/445; 424/443
(58) Field of Classification Search .............. None
See application file for complete search history.

(56) References Cited

U.S. PATENT DOCUMENTS

| | | | |
|---|---|---|---|
| 5,620,694 A | 4/1997 | Girardot | |
| 5,814,031 A * | 9/1998 | Mooney et al. | 604/307 |
| 6,221,382 B1 * | 4/2001 | Ishida et al. | 424/443 |
| 6,224,899 B1 * | 5/2001 | Misumi et al. | 424/448 |
| 6,432,431 B1 * | 8/2002 | Muta et al. | 424/402 |

FOREIGN PATENT DOCUMENTS

| | | |
|---|---|---|
| JP | 61-126018 | 6/1986 |
| JP | 5-717 | 1/1993 |
| JP | 06-022999 | 2/1994 |
| JP | 7-138154 | 5/1995 |
| JP | 7-44528 | 11/1995 |
| JP | 8-20530 | 1/1996 |
| JP | 08-119855 | 5/1996 |
| JP | 8-231385 | 9/1996 |
| JP | 10-67652 | 3/1998 |

(Continued)

OTHER PUBLICATIONS www.thefreedictionary.com/cataplasm defination.* English abstract of JP 8-104631 published Apr. 23, 1996.
English abstract of JP 7-313546 published Dec. 5, 1995.

(Continued)

*Primary Examiner* — Robert A Wax
*Assistant Examiner* — Melissa Mercier
(74) *Attorney, Agent, or Firm* — Wenderoth, Lind & Ponack, L.L.P.

(57) ABSTRACT

A thin aqueous cataplasm prepared by laminating an adhesive layer (base) having specified constituents on a support which consists of a fiber film prepared by heat-fusing a soft plastic resin on a composite fiber prepared by entangling a natural fiber and a soft plastic fiber, or consists of a fiber film prepared by heat-fusing a plastic resin having a soft part and a hard part in common on a fiber consisting of a plastic having a soft part and hard part in common.
The thin aqueous cataplasm retains a moisture-protecting effect on the skin and provides comfortable feeling in its use.

19 Claims, 2 Drawing Sheets

FOREIGN PATENT DOCUMENTS

| | | |
|---|---|---|
| JP | 11-12163 | 1/1999 |
| JP | 2000-117917 | 4/2000 |
| JP | 2003-12508 | 1/2003 |
| JP | 2003-181995 | 7/2003 |
| WO | 94/02674 | 2/1994 |
| WO | WO 94/02674 * | 2/1994 |

OTHER PUBLICATIONS

Supplementary European Search Report dated Dec. 16, 2009 in European Application No. EP 04 70 5178, which is a foreign counterpart of the present application.

* cited by examiner

THIN AQUEOUS CATAPLASM

TECHNICAL FIELD

The present invention relates to a thin aqueous cataplasm which can retain moisture-protecting effects on the skin and provides comfortable feeling in its use.

BACKGROUND ART

The cataplasm which has been used from of old is prepared by spreading a base containing mainly an aqueous polymer on a support such as an unwoven textile and the like. The base of the cataplasm is thick (700~1500 $g/m^2$). Therefore, the cataplasm is superior in adhesion to the skin. Furthermore, the initial moisture content in the base is much and the cataplasm can retain moisture-protection effects on the skin.

However, the traditional cataplasm requires a definite thickness in order to make adhesion forces exhibit. When it is applied to a much movable part like a joint, it may not follow the movement, or may be released owing to rub with cloth. When it is stuck for a long term, there is a problem that humidic retension may be lost. In order to solve these problems, it has been desired to make the cataplasm thin from the viewpoint of stability with the passage of time of the physical property and adequate improvement for the manufacturing process.

The present inventors tried to prepare thin aqueous cataplasms by using a known method for preparing cataplasms, and found as a result that these cataplasms had following demerits.

Namely, an unwoven textile and a woven textile which are well ventilated are used as a support of the traditional cataplasm and when the cataplasm is made thin, water in the cataplasm during application is evaporated by body temperature and the skin is not covered with enough moisture.

Furthermore, at the same time the base is dried by evaporation of water, and adhesion forces of the cataplasm to the skin decrease. On the other hand, adhesion to the skin extremely increases owing to solidification of the base on the applied portion and it gives pain and may occasionally give a slight injury to the skin when removing.

There are following problems: The support prepared by laminating a film having low ventilation with an unwoven textile or if necessary with an adhesive agent, by heat-fusing is inferior in flexibility and homogeneity, and the affinity of the base of the cataplasm is not enough. During application, since the cataplasm lacks in following the movement at the applied part, it is removed and when removing, the film may be tore or a part of the base remains to the skin.

Especially, any attention is not paid to the traditional cataplasms in regard to constituent of the support, constituents of the base and a combination thereof. For example, the amount of the base of the traditional cataplasms is increased (700~1500 $g/m^2$) to keep adequate adhesion forces, but these cataplasms are not prepared based on the plan fully suitable for thin aqueous cataplasms. Even if by simply making them thin (base 150~500 $g/m^2$), they-were not put in practice in the points of the simplicity of preparation, quality, skin tackiness and a change with the passage of time, or costs of preparation.

DISCLOSURE OF INVENTION

The object of the present invention provides thin aqueous cataplasm which can retain moisture-protecting effects on the skin and provide comfortable feeling in its use.

The present inventors have extensively studied constituents of a support (backing) and constituents of a base suitable for its support, and have found that a thin aqueous cataplasm prepared by spreading a base (at 150 to 500 $g/m^2$) which is prepared by mixing water, a moisture-retaining agent, polyacrylic acid and/or its salt, a cellulose derivative, a hardly soluble polyvalent metal salt and a pH controlling agent in their suitable rates, and by adjusting its pH to 4 to 6 on a support consisting of a fiber film (fiber having a film layer) prepared by heat-fusing a soft plastic resin on a composite fiber prepared by entangling a natural fiber and a soft plastic fiber, or on a support consisting of a fiber film prepared by heat-fusing a plastic resin having a soft part and a hard part in common on a fiber consisting of a plastic having a soft part and a hard part in common, could solve the above problems. Thus the present invention has been completed.

Namely, the present invention relates to a thin aqueous cataplasm prepared by laminating an adhesive layer (a base) on a support, and said support consisting of a fiber film prepared by heat-fusing a soft plastic resin on a composite fiber prepared by entangling a natural fiber and a soft plastic fiber, or consisting of a fiber film prepared by heat-fusing a plastic resin having a soft part and a hard part in common on a fiber consisting of a plastic having a soft part and hard part in common.

Furthermore concretely the present invention relates to a thin aqueous cataplasm having the above adhesive layer (base) which is essentially consisting of a tackifier consisting of water; a moisture-retaining agent and polyacrylic acid and/or its salt; an adhesion force-controlling agent consisting of a cellulose derivative; a crosslinking agent consisting of a hardly soluble polyvalent metal salt; and a pH controlling agent.

BEST MODE FOR CARRYING OUT THE INVENTION

Figure 1:
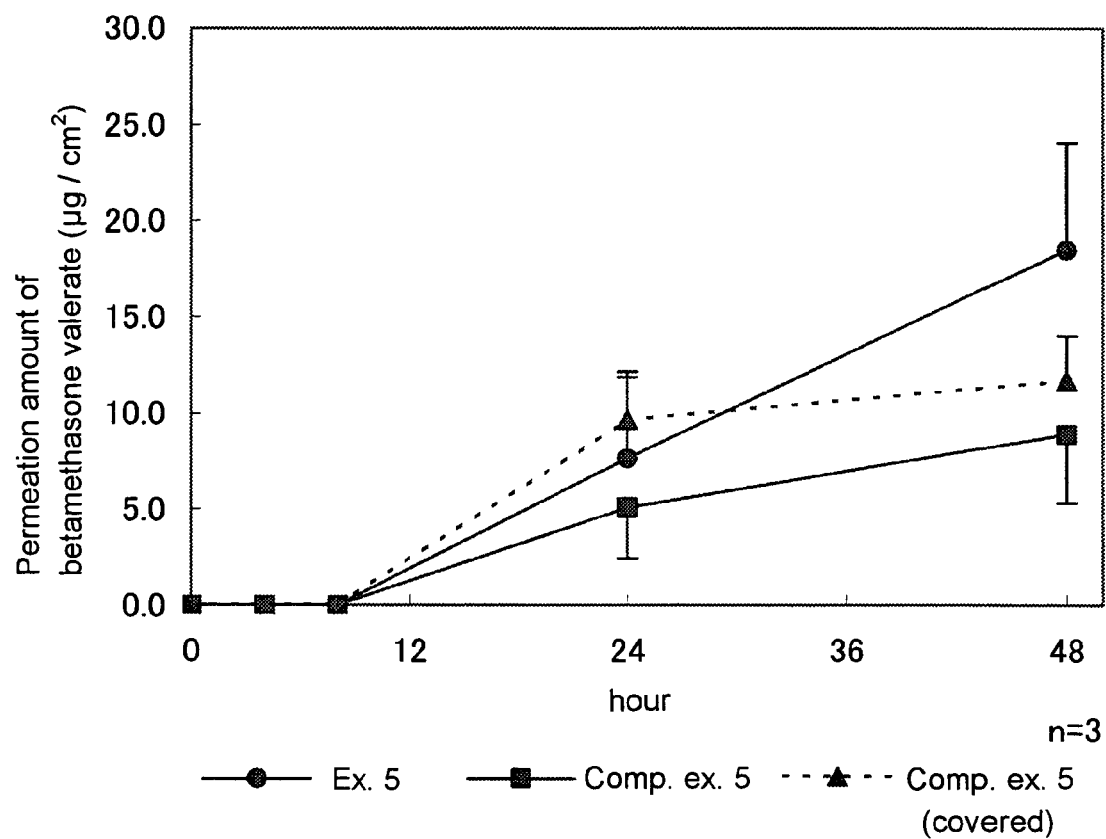
FIG. 1: The amount of betamethasone valerate penetrated via skin of a rat.

The composite fiber prepared by entangling a natural fiber and a soft plastic fiber used as the support related to the present invention is prepared by entangling the natural fiber and the soft plastic fiber at the rate of 1:9 to 9:1, preferably 2:8 to 8:2, especially preferably 3:7 to 7:3, mechanically in the range of its weight, 5 to 50 $g/m^2$, preferably 7 to 40 $g/m^2$, especially preferably 10 to 30 $g/m^2$.

The support related to the present invention is prepared by heat-fusing the soft plastic resin on the composite fiber in a film, in the rage of 3 to 35 μm in thickness, preferably 5 to 30 μm, especially preferably 8~25 μm. In this case, by using a composite fiber without a unitary fiber and by suitably controlling the rate of fibers, the soft plastic fiber part of the composite fiber is strongly fused on the soft plastic film when heat-fusing and enough amount of the natural fiber is exposed on the surface without fusing to the film. As a result, its affinity with the base becomes extremely strong.

The natural fiber used in the present specification (text) includes a semi synthetic or regenerated fiber derived from a natural fiber such as rayon, cotton, etc.

The soft plastic fiber includes polyethylene, polypropylene, ethylene methyl methacrylate, vinyl chloride and so on, especially preferably polyethylene and polypropylene.

The soft plastic resin includes polyethylene, ethylene methyl methacrylate, polypropylene and so on, especially preferably polyethylene and ethylene methyl methacrylate.

When the rate of the natural fiber is beyond 90 w/w % in the composite fiber (the rate of the soft plastic fiber is less than 10%), the fusion with the composite fiber and the film part is not enough. When the rate of the soft plastic fiber is beyond 90 w/w % (the rate of the natural fiber is less than 10 w/w %), the amount of the exposed natural fiber is not enough, the affinity with the base decreases, and especially when removing, the problem that the base is remained to skin occurs.

Irrespective of the rate of the natural fiber and the soft plastic fiber, when weight of the composite fiber is less than 5 $g/m^2$, the affinity with the base decreases. When it is beyond 50 $g/m^2$, the amount of the composite fiber becomes too much, the base is filled in the fiber, the adhesion forces decrease and therefore, a thin cataplasm can not be prepared.

When thickness of the film of the soft plastic resin which is heat-fused is less than 3 µm, the fusion with the composite fiber is not enough and the support containing the film is easily tore when removing. When it is beyond 35 µm, the cataplasm in which it is used is not thin, especially lucks in following the movement at the stuck (applied) part and the cataplasm is easily released.

Furthermore, as other support related to the present invention, can be used a fiber film prepared by heat-fusing a plastic resin having a soft part and a hard part in common on a fiber consisting of a plastic having a soft part and a hard part in common.

The fiber consisting of a plastic having a soft part and a hard part in common is prepared by entangling them mechanically in the range of its weight, 10 to 80 $g/m^2$, preferably 15 to 70 $g/m^2$, especially preferably 20 to 60 $g/m^2$.

Other support related to the present invention is prepared by heat-fusing on the above fiber, the plastic resin having the hard part and the soft part in common in a film having 7 to 70 µm in thickness, preferably 10 to 60 µm, especially preferably 15 to 45 µm. In this case, it is important to set up of the machine for fusing, and by using a not unitary plastic having a soft part and a hard part in common in both the fiber part and the plastic resin, and by suitably adjusting the weight and thickness of the fiber, a support useful for a thin aqueous cataplasm can be obtained. Namely, when heat-fusing, the soft parts contained in the fiber and the film strongly fuse together, and the same time, owing to the presence of the hard parts in the fiber and the film, it is protected that the fiber is excessively filled in (taken in) the film and the fiber is exposed enough on the surface, and the affinity with the base becomes stronger.

As the plastic part presenting in common in both of the fiber and the film, are preferably used a polymer elastomer, especially a polyamide elastomer and a polyester elastomer.

When weight of the fiber consisting of the plastic having a soft part and a hard part in common is less than 10 $g/m^2$, the affinity of the support with the base decreases and especially when removing the cataplasm, the base is remained to the skin. When it is beyond 80 $g/m^2$, the fiber is too much, the base is filled in the fiber, the adhesion forces decrease, and a thin cataplasm having enough adhesion forces can not be obtained.

When thickness of the plastic film having a hard part and a soft part in common which is fused by heating is less than 7 µm, the fusion with the fiber is weak, and the support containing it is easily tore when removing. Furthermore, when it is beyond 70 µm, the support lucks in flexibility, and the cataplasm in which it is used lucks in following the movement on the applied part and is easily released.

The constituents of the adhesive layer related to the present invention, namely the constituents of the base essentially consists of water, a moisture-retaining agent, polyacrylic acid and/or its salt, a cellulose derivative, a hardly soluble polyvalent metal salt, and a pH controlling agent. And by homogenously mixing these ingredients and by expanding the mixture on the support related to the present invention at the rate of 150~500 $g/m^2$ to prepare thin aqueous cataplasms which are rich in the affinity with the base.

The present invention has been made as a result of an extensive study on constituents of a support (backing) and constituents of a base suitable for its support, and when the constituents of the base and their rates are out side of the range mentioned below, the physical property of the base becomes extreme, the adhesion forces and the form-preservation (strength) become worse and furthermore, the affinity with the support related to the present invention becomes weak (worse).

The constituents of the base are explained below.

One of constituents of the adhesive layer, namely water is a medium to dissolve polyacrylic acid and/or its salt and a cellulose derivative and to give moisture to the skin.

The amount of water is 20 to 70 w/w %, preferably 25 to 60 w/w %, especially preferably 30 to 50 w/w %. When the amount of water is less than 20 w/w %, a polyacrylic acid derivative and a cellulose derivative are not well dissolved to be heterogeneous, the adhesion forces and the form-preservation of the base are not enough, and the moisture-retension to the skin decreases. When the amount of water is beyond 70 w/w %, the form-preservation of the base becomes unfavorably weak.

The moisture retaining agent has a function to raise the moisture-retaining effect and to control the form-preservation of the base. The moisture-retaining agent includes glycerin, 1,3-butyleneglycol, propylene glycol, polypropylene glycol, D-sorbitol, polyethylene glycol 400 and so on, especially preferably glycerin, 1,3-butylene glycol, propylene glycol.

The amount of it is 20 to 60 w/w %, preferably 25 to 55 w/w %, especially preferably 30 to 50 w/w %. When the amount is less than 20 w/w %, the form-preservation of the base lacks, and further the moisture-retention to the skin decreases. On the other hand, when the amount is beyond 60 w/w %, the amount of other ingredients, especially the amount of water lacks, the adhesion forces and the form-preservation of the base become unfavorably worse.

Polyacrylic acid and/or its salt have a function to raise the adhesion forces of the base owing to tackifier-function and crosslinking formation in case of dissolving them in water.

Polyacrylic acid and/or its salt include polyacrylic acid, sodium polyacrylate and a neutralized compound of polyacrylic acid, and they may used solely or in a mixture thereof. The amount of them is 3 to 25 w/w %, preferably 5 to 20 w/w %, especially preferably 7 to 15 w/w %. When the amount is less than 3 w/w %, the adhesion forces of the base decreases. When the amount is beyond 25 w/w %, insoluble materials occur, the base becomes heterogeneous and the constant adhesion forces are not maintained.

The cellulose derivative has a function to control the form-preservation of the base owing to thickening activity in case of dissolving it in water as an adhesion controlling agent. The cellulose derivative includes carboxymethyl cellulose sodium, hydroxypropyl cellulose, hydroxymethyl cellulose, and so on, or a mixture thereof, especially preferably carboxymethyl cellulose sodium. The amount of it is 1 to 20 w/w %, preferably 2 to 15 w/w %, especially preferably 3 to 10 w/w %. When the amount is less than 1 w/w %, the adhesion is low and the form-preservation of the base is not maintained. When the amount is beyond 20 w/w %, insoluble materials in water occur and the base becomes heterogeneous and the form-preservation of the base is not maintained.

The hardly soluble polyvalent metal salt makes a cross-link with a polyacrylic acid derivative as a cross-linking agent, to retain the form-preservation. The hardly soluble polyvalent metal salt includes dihydroxy aluminum aminoacetate, magnesium alminomethasilicate, aluminum hydroxide, synthetic hydrotalcite, especially preferably dihydroxy aluminum aminoacetate, synthetic hydrotalcite.

The amount of it is 0.01 to 5 w/w %, preferably 0.015 to 3.5 w/w %, especially preferably 0.03 to 2 w/w %. When the amount is less than 0.01 w/w %, the formation of the cross-linkage is not enough, and the form-preservation of the base becomes worse. When the amount is beyond 5 w/w %, the cross-linkage increases and the adhesion is worse.

The pH controlling agent is added to adjust pH of the base. The pH controlling agent includes tartaric acid, lactic acid, malic acid, etc.

The cataplasm of the present invention is intended to be applied for a long term. As the skin may be much injured by a strong acid or a strong basic substance, it is necessary to keep pH of the base adequately. The preferable pH thereof is a range of 4 to 6. Therefore, according to the amount of the substances such as polyacrylic acid which give an effect to pH of the base, the pH controlling agent is required to add 0.1 to 5 w/w %, preferably 0.25 to 3.5 w/w %, especially preferably 0.5 to 2 w/w % thereto.

The amount of the base which is spread and laminated on the support related to the present invention is 150 to 500 g/m$^2$, preferably 200 to 450 g/m$^2$, especially preferably 250 to 400 g/m$^2$.

Thus prepared cataplasms of the present invention are cut in suitable size and form according to the applied part and are used thereto.

In the above base a medicine having therapeutic effects may be contained. The medicine is not limited as far as it can be stably mixed in the base, for example, antiinflammatory analgesics, corticosteroids (triamcinolone, betamethasone valerate, etc.), antihistamines, antipruritics, antihypertensives, anesthetics, antifungals, antiepileptics, coronal vasodilator, hormones, muscle relaxants, topical stimulants, antiviral agent (aciclovir, etc.), etc.

As the cataplasm of the present invention contains water, a stabilizer, a preservative and so on may be contained in order to stabilize the base itself or the medicine which is contained therein.

The cataplasm of the present invention can be used also in order to cover (protect) the injured lesion.

EXAMPLE

The examples are illustrated in order to explain the present invention, but the present invention should not be limited by these examples.

Example 1

The cataplasm was prepared by the following procedures according to constituents of the base shown in Example 1 of Table 1.

To glycerin (39 w/w %) were added sodium polyacrylate (4 w/w %), carboxymethyl cellulose sodium (4.5 w/w %), hydroxypropyl cellulose (0.5 w/w %), dihydroxyaluminum aminoacetate (0.06 w/w %) to disperse them (Dispersed solution 1). To purified water (42.44 w/w %) were added tartaric acid (1.5 w/w %) and polyacrylic acid (5 w/w %) to dissolve them. To this solution was gradually added the dispersed solution 1 under stirring, and the mixture was stirred until the mixture became a homogenous lump to give a base.

This base was spread on a support consisting of constituents for the support shown in Example 1 of Table 1 so that weight of base was 300 g/m$^2$, and the adhesive surface (surface of the base) was covered by a polyester film, and it was punched in a size of 20 cm×20 cm (square) to give a cataplasm. The cataplasms were put in a wrapping bag, sealed and stored at room temperature.

Examples 2 to 4 and Comparative Examples 1 to 4

Cataplasms of Examples 2 to 4 and Comparative examples 1 to 4 were prepared by the same procedure as Example 1 according to each constituents shown in Tables 1 and 2.

TABLE 1

| Base | Example 1 | Example 2 | Example 3 | Comparative ex. 1 | Comparative ex. 2 | Comparative ex. 3 |
|---|---|---|---|---|---|---|
| | (w/w %) | | | | | |
| Purified water | 42.44 | 50.44 | 43.24 | 42.44 | 50.44 | 43.24 |
| Glycerin | 39 | 25 | 30 | 39 | 25 | 30 |
| 1,3-Butylene glycol | 3 | | 1 | 3 | | 1 |
| Propylene glycol | | 10 | 5 | | 10 | 5 |
| Polyacrylic acid | 5 | 3 | 7 | 5 | 3 | 7 |
| Sodium polyacrylate | 4 | 3 | 3 | 4 | 3 | 3 |
| Neutralized polyacrylic acid | | 2 | 1 | | 2 | 1 |
| Carboxymethylcellulose sodium | 4.5 | 3 | | 4.5 | 3 | |
| Hydroxypropyl cellulose | 0.5 | | 5 | 0.5 | | |
| Hydroxymethyl cellulose sodium | | 2 | 2 | | 2 | |
| Magnesium alminomethasilicate | | 0.2 | | | 0.2 | |
| Dihydroxyaluminum aminoacetate | 0.06 | 0.06 | 0.06 | 0.06 | 0.06 | 0.06 |
| Hydroxyaluminium | | | 2 | | | 2 |
| Tartaric acid | 1.5 | 1 | 0.5 | 1.5 | 1 | 0.5 |
| Lactic acid | | 0.3 | 0.2 | | 0.3 | 0.2 |
| Malic acid | | | 0.3 | | | 0.3 |

TABLE 1-continued

| Base | Example 1 | Example 2 | Example 3 | Comparative ex. 1 (w/w %) | Comparative ex. 2 | Comparative ex. 3 |
|---|---|---|---|---|---|---|
| Constituent of fiber | | | | | | |
| Rayon fabric | 60% | 50% | | 100% | 60% | 60% |
| Cotton fabric | | | 30% | | | |
| Polyethylene fabric | 28% | 50% | 70% | | 28% | 28% |
| Polypropyrene fabric | 12% | | | | 12% | 12% |
| Weight | 18 g/m² | 10 g/m² | 25 g/m² | 3 g/m² | 18 g/m² | 25 g/m² |
| Soft plastic resin-film | | | | | | |
| Ethylene methyl methacrylate resin | 15 μm | | 10 μm | 15 μm | | 10 μm |
| Polyethylene resin | | 20 μm | | | 80 μm | |
| pH of base | 4.3 | 5 | 4.5 | 4.3 | 5 | 4.4 |
| Weight of base | 300 g/m² | 350 g/m² | 230 g/m² | 300 g/m² | 400 g/m² | 350 g/m² |

TABLE 2

| Constituent of base | Example 4 | Comparative example 4 |
|---|---|---|
| | (w/w %) | |
| Purified water | 42.41 | 42.56 |
| Glycerin | 39 | 39 |
| 1,3-Butylene glycol | 3 | 3 |
| Polyacrylic acid | 5 | 5 |
| Sodium polyacrylate | 4 | 4 |
| Carboxymethylcellulose sodium | 4.3 | 4.3 |
| Hydroxypropyl cellulose | 0.5 | 0.5 |
| Dihydroxyaluminum aminoacetate | 0.06 | 0.06 |
| Tartaric acid | 1.5 | 1.5 |
| Sodium edatate | 0.08 | 0.08 |
| Propylparaben | 0.1 | |
| Methylparaben | 0.05 | |
| Support | | |
| Fiber (polyamide elastomer) | Weight: 40 g/m² | Weight: 2 g/m² |
| Film (polyamide elastomer) | Thickness: 15 μm | Thickness: 10 μm |
| Weight of base | 350 g/m² | 350 g/m² |

Example 5

A cataplasm was prepared by further adding betamethasone valerate (0.1 w/w %) as a medicine to constituents of the paste of Example 1.

Example 6

A cataplasm was prepared by further adding aciclovir (5 w/w %) as a medicine to the ingredients of the paste of Example 1.

Comparative Example 5

A commercialized ointment containing betamethasone valerate (0.12 w/w %) as a medicine.

Comparative Example 6

A commercialized ointment containing aciclovir (5 w/w %) as a medicine.

Test 1

The preparations of Examples 1 to 4 and Comparative examples 1 to 4 were cut in a size of 7.5 cm×10 cm to use them as a test sample, respectively. To three healthy adult (male) persons was applied the test sample (one piece) for 8 hours, the observation was done during application and when removing, and the result was shown in Table 3.

From this result, in regard to the preparations of Comparative examples, the release of the sample during application was much and when removing, tear of the support and separation between the base and the support or separation between the fiber and the film in the support occurred, and the base or the sample was remained to the arm. Thus these samples did not succeed in the preparation of the present invention.

On the other hand, in regard to the preparations of Examples, the release of the sample during application was less and when removing the base or the sample was less remained to the arm. Thus it was revealed that all of these samples had functions suitable for the preparation of the present invention.

TABLE 3

| Test sample | Volunteer No. 1 | No. 2 | No. 3 |
|---|---|---|---|
| Example 1 | No releasing during application and no base remained to applied arm when releasing. | No releasing during application and no base remained to applied arm when releasing. | About 5% of applied area was released during application. Base was not remained to arm when releasing. |
| Example 2 | About 15% of applied area was released during application. Support and base were slightly separated and about 10% of base was remained to arm when releasing. | No releasing during application and no base remained to applied arm when releasing. | About 10% of applied area was released during application. Base was not remained to arm when releasing. |
| Example 3 | No releasing during application and no base remained to applied arm when | About 10% of applied area was released before releasing. Base was not | Releasing during application was slight. Support and base were |

TABLE 3-continued

| Test sample | Volunteer No. 1 | No. 2 | No. 3 |
|---|---|---|---|
| | releasing. | remained to arm when releasing. | slightly separated and about 15% of base was remained to arm when releasing |
| Example 4 | About 15% of applied area was released during application. Base was not remained to arm when releasing. | No releasing during application and no base remained to applied arm when releasing. | No releasing during application and no base remained to applied arm when releasing. |
| Comparative ex. 1 | About 30% of applied area was released during application. Support and base were separated and most base was remained to arm when releasing. | No releasing during application. Support and base, and film and fiber of support were separated and most base was remained to arm when releasing. | About 5% of applied area was released during application. Support and base were separated and most base was remained to arm when releasing. |
| Comparative ex. 2 | Sample came off 6 hr later after application. | About 70% of applied area was released during application. Base was not remained to arm when releasing. | Sample came off 7 hr later after application. |
| Comparative ex. 3 | Sample came off 2 hr later after application. At that time base layer was separated and about 80% of base was remained to arm. | Sample came off 4 hr later after application. At that time base layer was separated and about 70% of base was remained to arm. | Sample came off 5 hr later after application. At that time base layer was separated and most base was remained to arm. |
| Comparative ex. 4 | No releasing during application. Support was tore and sample was remained to arm when releasing. | No releasing during application. Support and base were separated and support was tore and sample was remained to arm when releasing. | About 10% of applied area was released during application. Support was tore and sample was remained to arm when releasing. |

Test 2

Test 2-1

[Test Method]

To the pathologic lesions, symmetrical two parts, of a patient suffering psoriasis, an ointment containing triamcinolone (0.1 w/w %) (commercialized) was applied twice a day for 2 weeks. In regard to one part, the preparation of Example 4 was stuck on and covered (occluded) over the ointment applied. Every time the ointment was applied, the occlusion with the preparation of Example 4 was done over. The other part was served as a control without sticking the preparation of Example 4.

For 4 weeks from starting therapy, the pathologic lesions were observed in change with the passage of time and the evaluation was done in accordance with the following standard.

[Standard for Judging]

TABLE 4

Standard for judging (1): Symptom showing stimulation of skin such as erythema

| Score | Standard | Symptom |
|---|---|---|
| 0 | Normal | Normal (no rash) |
| 1 | Mild | Slight rash on the lesion |
| 2 | Moderate | Rash on the lesion |
| 3 | Severe | Fairly rash on the lesion |
| 4 | Very severe | Remarkable rash on the lesion |

TABLE 5

Standard for judging (2): Symptom wherein a part of the skin is elevated from other skin like papule

| Score | Standard | Symptom |
|---|---|---|
| 0 | Normal | Normal (no elevation) |
| 1 | Mild | Slight elevation on the lesion |
| 2 | Moderate | Part around the lesion was moderately elevated with rounded or sloped edges. |
| 3 | Severe | Part around the lesion was markedly elevated. |

TABLE 5-continued

Standard for judging (2): Symptom wherein a part of the skin is elevated from other skin like papule

| Score | Standard | Symptom |
|---|---|---|
| 4 | Very severe | Part around the lesion was very markedly elevated. |

TABLE 6

Standard for judging (3): Symptom like surface of the skin is rough as scale

| Score | Standard | Symptom |
|---|---|---|
| 0 | Normal | Normal (no scaling) |
| 1 | Mild | Scale occurred and partially covered the lesion. |
| 2 | Moderate | Coarse scale occurred and partially covered the lesion. |
| 3 | Severe | Thick, rough scale occurred and covered all lesion. |
| 4 | Very severe | Very thick, very rough scale occurred and covered all lesion. |

Example of Calculation of Scores:

Score 9=score 3 (severe) at standard (1)+score 2 (moderate) at standard (2)+score 4 (very severe) at standard (3)

TABLE 7

[Result]

| Test subject | Score (one day) | Score (one week) | Score (two weeks) | Score (four weeks) |
|---|---|---|---|---|
| No. 1 | 8.5/8.5 | 3.5/8.0 | 2.5/6.0 | 2.5/6.0 |
| No. 2 | 6.5/6.0 | 3.0/5.5 | 2.0/4.0 | 6.0/7.0 |

Score: Preparation of Example 4 was stuck and occluded/un-occluded.

Test 2-2

This test was carried out in the same way as Test 2-1 except for using an ointment of clobetasol (0.05 w/w %) (commercialized).

TABLE 8

| | [Result] | | | |
|---|---|---|---|---|
| Test subject | Point (one day) | Point (one week) | Point (two weeks) | Point (four weeks) |
| No. 1 | 5.5/5.5 | 3.5/4.0 | 1.5/1.5 | 1.0/2.5 |

Point: Preparation of Example 4 was stuck and occluded/un-occluded.

Test 2-3
[Test Method]

To the pathologic lesions, symmetrical two parts, of a patient suffering psoriasis, only a preparation of Example 4 was applied twice a day for 2 weeks to one part. The other part was served as a control without using any ointment and the preparation of Example 4.

For 4 weeks from starting therapy, the pathologic lesions were observed in change with the passage of time and the evaluation was done in accordance with the following standard.

TABLE 9

| | [Result] | | | |
|---|---|---|---|---|
| Test subject | Score (one day) | Score (one week) | Score (two weeks) | Score (four weeks) |
| No. 1 | 6.5/6.5 | 4.5/6.0 | 5.0/7.0 | 5.5/7.0 |
| No. 2 | 5.0/4.5 | 3.0/5.5 | 2.0/5.0 | 4.5/5.5 |

Point: Preparation of Example 4 was stuck and occluded/un-occluded.

From the results of Tests 2-1 and 2-2, when the ointment containing a medicine was applied (spread) on the pathogenic lesion and thereon the preparation of Example 4 was stuck, the therapeutic effect was increase and was sustained. According to Test 2-3, the preparation of Example 4 solely showed therapeutic effect without other ointment.

Therefore, it was suggested that the cataplasm of the present invention further promoted effects of the medicine in the base and it had effects even if using only the cataplasm, owing to the specific function of a thin aqueous cataplasm.

Test 3

The skin extracted from the abdomen of a rat was fit on Frantz-diffusion cell, and the preparation of Example 5 (test drug) was punched in a circle having a diameter 15 mm (containing betamethasone valerate 53 µg) and the test drug was stuck on the skin on the diffusion cell. On the other hand, the ointment of Comparative example 5 (44 mg) (containing betamethasone valerate 53 µg) was spread on the skin of the rat on the diffusion cell and a half of the surface of the ointment was covered with a polyester film. On the receptor side, 30% isopropyl alcohol-phosphate buffer was used and the receptor solution was taken at regular intervals, and the concentration of betamethasone valerate in the taken solution was measured by HPLC, and the medicine permeated via the skin was calculated. The result was shown in FIG. 1.

From this test result, the preparation of Example 5 showed higher permeation of the drug than the ointment of Comparative example 5 (commercialized) and showed the same or more sustaining than said ointment covered by a polyester film.

From this fact, it was suggested that the cataplasm of the present invention was useful even if a medicine (corticosteroid) was contained.

Test 4

Figure 2:
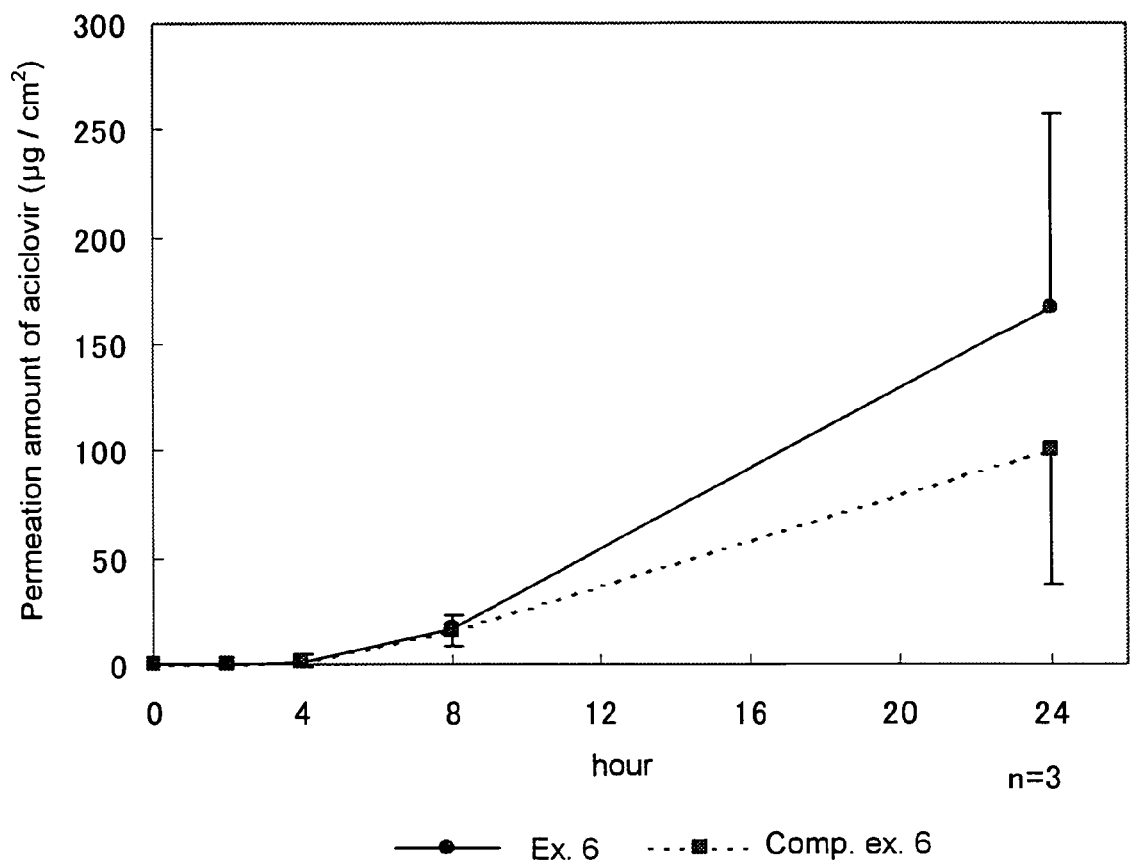
FIG. 2: The amount of aciclovir penetrated via skin of a rat.

The skin extracted from the abdomen of a rat was fit on Frantz-diffusion cell, and the preparation of Example 6 (test drug) was punched in a circle having a diameter 15 mm (containing aciclovir 2.6 mg) and the test drug was stuck on the skin on the diffusion cell. On the other hand, the ointment of Comparative example 6 (52 mg) (containing acyclovir 2.6 mg) was spread on the skin of the rat on the diffusion cell and a half of the surface of the ointment was covered with a polyester film. On the receptor side, phosphate buffer was used and the receptor solution was taken at regular intervals, and the concentration of acyclovir in the taken solution was measured by HPLC, and the medicine permeated via the skin was calculated. The result was shown in FIG. 2.

From this test result, the preparation of Example 6 showed higher permeation of the drug than the ointment of Comparative example 6 (commercialized).

From this fact, it was suggested that the cataplasm of the present invention was useful even if a medicine (an antiviral agent) was contained.

INDUSTRIAL APPLICABILITY

The thin aqueous cataplasm of the present invention can be prepared by laminating thin a base at 150 to 500 g/m² on a support by using as a base, an adhesive agent essentially consisting of water, a moisture-retaining agent, a polyacrylic acid derivative (tackifier), a cellulose derivative (adhesion force-controlling agent), a hardly soluble polyvalent metal salt and a pH controlling agent, and by using as a support, a fiber film prepared by heat-fusing in a film a soft plastic resin on a composite fiber prepared by entangling a natural fiber and a soft plastic fiber, or a fiber film prepared by heat-fusing a plastic resin having a soft part and a hard part in common on a fiber consisting of a plastic having a soft part and a hard part in common, and therefore, can show the following superior effects comparing with the traditional cataplasm.

(1) The cataplasm of the present invention has sufficient adhesion forces, is excellent in following the movement of the applied portion, the evaporation from the support is protected and therefore, the moisture-retention to the skin can be sustained for a long term. Furthermore, when a medicine is contained in the cataplasm of the present invention, or the cataplasm is covered after a base (ointment) in which a medicine is dissolved or dispersed is spread on the skin, the therapeutic effect is promoted and retained owing to the moisture retaining effect for a long term.

(2) The moisture in the base is maintained without decrease, and the adhesion forces and the form-preservation were preferably maintained and therefore, the quality of it can be stably maintained for a long term.

(3) The amount of the base is decreased and the cataplasm is made thin and therefore, the adequateness of the process for preparation progresses and furthermore, cost for manufacturing, preservation and business-distribution can be decreased.

The invention claimed is:

1. A thin aqueous cataplasm prepared by only laminating an adhesive layer on a support, and said support consisting of a fiber film having a thickness in a range of 3-35 µm prepared by heat-fusing a soft plastic resin on a composite fiber prepared by entangling a natural fiber and a soft plastic fiber, or said support consisting of a fiber film having a thickness in a range of 7-70 µm prepared by heat-fusing a plastic resin having a soft part and a hard part in common on a fiber consisting of a plastic having a soft part and hard part in common, and said adhesive layer consisting of 25 to 60 w/w % of water, a moisture-retaining agent, polyacrylic acid and/or its salt, a cellulose derivative selected from the group consisting of carboxymethyl cellulose sodium, hydroxypropyl cellulose and hydroxymethyl cellulose, a slightly soluble polyvalent metal salt and a pH controlling agent, and its pH is adjusted to 4 to 6.

2. The thin aqueous cataplasm claimed in claim 1 wherein the support consists of a fiber film prepared by heat-fusing a soft plastic resin on a composite fiber prepared by entangling a natural fiber and a soft plastic fiber.

3. The thin aqueous cataplasm claimed in claim 1 wherein the support consists of a fiber film prepared by heat-fusing a plastic resin having a soft part and a hard part in common on a fiber consisting of a plastic having a soft part and hard part in common.

4. The thin aqueous cataplasm claimed in claim 1 wherein weight of the adhesive layer laminated on the support is 150 to 500 g/m$^2$.

5. The thin aqueous cataplasm claimed in claim 2 wherein the support consists of a fiber film prepared by heat-fusing a soft plastic resin selected from polyethylene and ethylene methyl methacrylate on a composite fiber prepared by entangling a natural fiber selected from rayon and cotton, and a soft plastic fiber selected from polyethylene and polypropylene.

6. The thin aqueous cataplasm claimed in claim 1 wherein the support consists of a fiber film prepared by heat-fusing a plastic resin having a soft part and a hard part in common selected from polyamide elastomer and polyester elastomer on a fiber consisting of a plastic having a soft part and hard part in common selected from polyamide elastomer and polyester elastomer.

7. The thin aqueous cataplasm claimed in claim 1 wherein the adhesive layer consists of 25 to 60 w/w % water; 25 to 55 w/w % of a moisture-retaining agent selected from glycerin, 1,3-butyleneglycol and propyleneglycol; 5 to 20 w/w % polyacrylic acid and/or its salt; 2 to 15 w/w % of a cellulose derivative selected from carboxymethyl cellulose sodium, hydroxypropyl cellulose and hydroxymethyl cellulose; 0.015 to 3.5 w/w % of a slightly soluble polyvalent metal salt selected from dihydroxy aluminum aminoacetate, magnesium alminomethasilicate, aluminum hydroxide and synthetic hydrotalcite; and 0.25 to 3.5 w/w % of a pH controlling agent.

8. The thin aqueous cataplasm claimed in claim 3 wherein the adhesive layer consists of water, a moisture-retaining agent, polyacrylic acid and/or its salt, a cellulose derivative, a hardly soluble polyvalent metal salt and a pH controlling agent, and its pH is adjusted to 4 to 6.

9. The thin aqueous cataplasm claimed in claim 2 wherein weight of the adhesive layer laminated on the support is 150 to 500 g/m$^2$.

10. The thin aqueous cataplasm claimed in claim 3 wherein weight of the adhesive layer laminated on the support is 150 to 500 g/m$^2$.

11. The thin aqueous cataplasm claimed in claim 4 wherein the support consists of a fiber film prepared by heat-fusing a soft plastic resin selected from polyethylene and ethylene methyl methacrylate on a composite fiber prepared by entangling a natural fiber selected from rayon and cotton, and a soft plastic fiber selected from polyethylene and polypropylene.

12. The thin aqueous cataplasm claimed in claim 3 wherein the support consists of a fiber film prepared by heat-fusing a plastic resin having a soft part and a hard part in common selected from polyamide elastomer and polyester elastomer on a fiber consisting of a plastic having a soft part and hard part in common selected from polyamide elastomer and polyester elastomer.

13. The thin aqueous cataplasm claimed in claim 4 wherein the support consists of a fiber film prepared by heat-fusing a plastic resin having a soft part and a hard part in common selected from polyamide elastomer and polyester elastomer on a fiber consisting of a plastic having a soft part and hard part in common selected from polyamide elastomer and polyester elastomer.

14. The thin aqueous cataplasm claimed in claim 2 wherein the adhesive layer consists of 25 to 60 w/w % water; 25 to 55 w/w % of a moisture-retaining agent selected from glycerin, 1,3-butyleneglycol and propyleneglycol; 5 to 20 w/w % polyacrylic acid and/or its salt; 2 to 15 w/w % of a cellulose derivative selected from carboxymethyl cellulose sodium, hydroxypropyl cellulose and hydroxymethyl cellulose; 0.015 to 3.5 w/w % of a slightly soluble polyvalent metal salt selected from dihydroxy aluminum aminoacetate, magnesium alminomethasilicate, aluminum hydroxide and synthetic hydrotalcite; and 0.25 to 3.5 w/w % of a pH controlling agent.

15. The thin aqueous cataplasm claimed in claim 3 wherein the adhesive layer consists of water (20 to 60 w/w %); a moisture-retaining agent (25 to 55 w/w %) selected from glycerin, 1,3-butyleneglycol and propyleneglycol; polyacrylic acid and/or its salt (5 to 20 w/w %); a cellulose derivative (2 to 15%) selected from carboxymethyl cellulose sodium, hydroxypropyl cellulose and hydroxymethyl cellulose; a hardly soluble polyvalent metal salt (0.015 to 3.5 w/w %) selected from dihydroxy aluminum aminoacetate, magnesium alminomethasilicate, aluminum hydroxide and synthetic hydrotalcite; and a pH controlling agent (0.25 to 3.5 w/w %).

16. The thin aqueous cataplasm claimed in claim 4 wherein the adhesive layer consists of 25 to 60 w/w % water; 25 to 55 w/w % of a moisture-retaining agent selected from glycerin, 1,3-butyleneglycol and propyleneglycol; 5 to 20 w/w % polyacrylic acid and/or its salt; 2 to 15 w/w % of a cellulose derivative selected from carboxymethyl cellulose sodium, hydroxypropyl cellulose and hydroxymethyl cellulose; 0.015 to 3.5 w/w % of a slightly soluble polyvalent metal salt selected from dihydroxy aluminum aminoacetate, magnesium alminomethasilicate, aluminum hydroxide and synthetic hydrotalcite; and 0.25 to 3.5 w/w % of a pH controlling agent.

17. The thin aqueous cataplasm claimed in claim 5 wherein the adhesive layer consists of 30 to 50 w/w % water; 25 to 55 w/w % of a moisture-retaining agent selected from glycerin, 1,3-butyleneglycol and propyleneglycol; 5 to 20 w/w % polyacrylic acid and/or its salt; 2 to 15 w/w % of a cellulose derivative selected from carboxymethyl cellulose sodium, hydroxypropyl cellulose and hydroxymethyl cellulose; 0.015 to 3.5 w/w % of a slightly soluble polyvalent metal salt selected from dihydroxy aluminum aminoacetate, magnesium alminomethasilicate, aluminum hydroxide and synthetic hydrotalcite; and 0.25 to 3.5 w/w % of a pH controlling agent.

18. The thin aqueous cataplasm claimed in claim 6 wherein the adhesive layer consists of water (20 to 60 w/w %); a moisture-retaining agent (25 to 55 w/w %) selected from glycerin, 1,3-butyleneglycol and propyleneglycol; polyacrylic acid and/or its salt (5 to 20 w/w %); a cellulose derivative (2 to 15%) selected from carboxymethyl cellulose sodium, hydroxypropyl cellulose and hydroxymethyl cellulose; a hardly soluble polyvalent metal salt (0.015 to 3.5 w/w %) selected from dihydroxy aluminum aminoacetate, magnesium alminomethasilicate, aluminum hydroxide and synthetic hydrotalcite; and a pH controlling agent (0.25 to 3.5 w/w %).

19. A process for preparing a thin aqueous cataplasm which consists of the following steps (1) to (3):

(1) a process for preparing a composite fiber which comprises entangling a natural fiber and a soft plastic fiber in the range of 3-35 μm, (2) a process for preparing a support consisting of a fiber film which comprises heat-fusing a soft plastic resin on said composite fiber, and then (3) a process for preparing a thin aqueous cataplasm which comprises laminating an adhesive layer on said support, or the following steps (4) to (5):

(4) a process for preparing a support consisting of a fiber film which comprises heat-fusing a plastic resin having a soft part and a hard part in common on a fiber consisting of a plastic having a soft part and hard part in common in the range of 7-70 μm, and then (5) a process for preparing a thin aqueous cataplasm which comprises laminating an adhesive layer on the support prepared in step (4), wherein said adhesive layer consists of 25 to 60 w/w % of water, a moisture-retaining agent, polyacrylic acid and/or its salt, a cellulose derivative selected from the group consisting of carboxymethyl cellulose sodium, hydroxypropyl cellulose and hydroxymethyl cellulose, a slightly soluble polyvalent metal salt and a pH controlling agent, and has a pH of 4 to 6.

* * * * *